United States Patent [19]

Rogers

[11] Patent Number: 5,144,705
[45] Date of Patent: Sep. 8, 1992

[54] SEAT CUSHIONS INCLUDING A PLURALITY OF INDIVIDUAL SUPPORT CELLS

[76] Inventor: John E. Rogers, P.O. Box 1437, Blue Jay, Calif. 92317

[21] Appl. No.: 711,080

[22] Filed: Jun. 6, 1991

Related U.S. Application Data

[60] Division of Ser. No. 486,690, Mar. 1, 1990, Pat. No. 5,068,504, which is a continuation of Ser. No. 323,672, Mar. 15, 1989, abandoned.

[51] Int. Cl.$^5$ .............................................. A47C 20/02
[52] U.S. Cl. ........................................ 5/453; 5/455; 5/457; 5/654
[58] Field of Search ......... 297/284 B, 284 E, DIG. 3; 5/449, 453, 455, 456, 457, 476

[56] References Cited

U.S. PATENT DOCUMENTS

| | | | |
|---|---|---|---|
| 3,192,540 | 7/1965 | Swank | 5/456 |
| 3,608,961 | 9/1971 | Von Heck | 5/453 X |
| 4,067,078 | 1/1978 | Winston | 297/284 B |
| 4,186,734 | 2/1980 | Stratton | 5/453 X |
| 4,694,520 | 9/1987 | Paul et al. | 5/453 |

FOREIGN PATENT DOCUMENTS

1035000 7/1978 Canada ..................................... 5/449

Primary Examiner—Michael F. Trettel
Attorney, Agent, or Firm—Natan Epstein

[57] ABSTRACT

A seat cushion is provided that comprises a baseboard having an upper surface bounded by a forward edge, a rear edge, and two sides. A number of pressurized cells or bladders are attached to the upper surface and arranged in rows between the forward and rear edges, the rows are spaced apart to define a central depression between the rows. The cells can be independently and selectively pressurized by a fluid such as air such that the support characteristics of the cells can be adjusted to a desired body support profile. The cells are also physically spaced and mechanically decoupled such that deformation of one cell under load is not significantly transmitted to an adjacent cell. The cell spacing is such to provide body support primarily against the buttocks and thighs and to reduce pressure against the coccyx, anal, ischial, and genital areas of a user. The rearmost cells in the rows can be spaced so as to provide an ischial cavity for relieving pressure on the ischial tuberosity areas of a user.

5 Claims, 4 Drawing Sheets

SEAT CUSHIONS INCLUDING A PLURALITY OF INDIVIDUAL SUPPORT CELLS

This application is a divisional of application Ser. No. 07/486,690, filed Mar. 1, 1990, now U.S. Pat. No. 5,068,504, which is a continuation application of Ser. No. 07/323,672, filed Mar. 15, 1989 now abandoned.

BACKGROUND OF THE INVENTION

1. Field of the Invention

The present invention pertains generally to the field of body supporting and cushioning devices and more particularly relates to seat cushions and body supports directed to meet the needs of persons who are chair-bound for medical or other reasons over protracted periods of time, and diagnostic devices for properly fitting such cushions to the needs of particular individuals.

2. State of the Prior Art

Much inventive activity has been directed to the development of various cushioning and support devices for use by the handicapped, the chair-bound, the bed-ridden, and generally by non-ambulatory individuals. A recurrent problem encountered by such persons is the increased likelihood of ulceration and damage to skin and underlying tissues at areas of the body which are subjected to continuous moderate or high levels of pressure over periods of hours and sometimes days without relief. Such conditions lead to the formation of decubitus ulcers, commonly known as bed sores.

Protracted pressure against any portion of the skin has the effect of diminishing or cutting off peripheral vascular flow to that area. If impairment of blood flow to the affected area is sufficiently prolonged, the tissues underlying the affected skin area will be starved of nutrients and suffer progressive damage. Typically it is the underlying soft tissues which are first damaged, until eventually the skin undergoes necrosis and ulcerates in progressive manner, and unless the pressure on the area is removed, such ulcers can become deep open wounds which are difficult to treat and slow to heal.

Even moderate levels of pressure over relatively brief periods of time can lead to significant skin and tissue damage and much effort has therefore been expended towards providing improved seat cushions and backpads for non-ambulatory persons confined to wheel chairs. The difficulties encountered by such persons are frequently compounded by medical conditions which may insensitize the person to progressive skin and tissue damage until such damage has reached advanced and serious stages, and by conditions which deprive the individual of any ability to reposition him or herself so as to relieve continuous pressure on any particular portion of the anatomy to thus stem the formation of ulcerations or other soft tissue damage by periodically shifting position.

One anatomical area which is particularly susceptible to soft tissue damage in persons confined to a sitting position over protracted periods of time is the skin and soft tissue overlying and adjacent to the ischial tuberosities of the pelvis, and the sacral and coccyx areas, particularly in the case of those with spinal cord injury. In such cases, utmost care must be taken to minimize pressure levels on certain portions of the anatomy which are particularly susceptible to the formation of decubitus ulcers, and to distribute the pressures exerted by cushions or other body support devices in a manner which reduces peak pressure levels to acceptable levels considered to be relatively benign over longer periods of time.

There is a continuing need for more effective, simpler and easier to fit devices in furtherance of the above mentioned objectives.

SUMMARY OF THE INVENTION

In a first aspect of this invention, an improved seat cushion is provided particularly for use by the chair-bound, including a slab of compressible material having an upper seat surface, an undersurface, a forward edge, a rear edge and two side edges. An ischial cavity or recess is formed in the seat surface intermediate the side edges, which recess is open at the rear edge of the slab and extends from the rear edge partly or fully toward the forward edge. The ischial cavity is dimensioned for generally receiving the ischial tuberosity area of a person seated on the slab with the knees overhanging the forward edge, and the seat surface is dimensioned for providing substantial buttock supporting and thigh supporting areas laterally and forwardly of the ischial cavity, so that support is withdrawn from underneath the ischial and coccyx areas and the person's weight is substantially shifted onto the fleshy underside of the buttocks and thighs, and pressure relief is afforded the ischial tuberosity area.

The seat cushion constructed according to this aspect of the invention is characterized in that the ischial tuberosity area of a particular intended user is subjected to peak pressure within the ischial recess lesser than a predetermined pressure considered to be damaging over extended periods to body tissues in the ischial region. The cushion slab may typically measure between about 16 and 22 inches in length and width and about four inches in thickness, and the ischial cavity preferably measures at least six inches in length from the rear edge towards the forward edge, and is at least six inches wide at the rear edge. It is further desirable that the ischial cavity have its greatest width at the rear edge of the cushion slab, and taper to a forward end, as in a generally semi-elliptical, trapezoidal or triangular shape. An optional sensor element may be arranged in the ischial cavity for detecting excessive peak pressure levels on the ischial tuberosity of a person seated on the cushion slab.

A further feature of the improved cushion is provision of shear stress control at the edge of the ischial cavity on the seat surface. Such control is desirable to minimize or eliminate the shearing effect found at the boundary of a seat surface and a cavity or hole in a body supporting surface, caused by the tendency of soft tissues to extrude into a void in the supporting surface. Such control can be provided in the improved cushion by one or a combination of several approaches. In a first solution the ischial recess includes an edge surface sloping from the cavity edge into the recess at an angle such as to provide graduated support and reduced shear stress in the vicinity of the edge to the body of a person seated on the seat surface. The edge surface may slope from the edge toward the center of the cavity or from the edge away from the center of the cavity to undercut the edge. In a second solution small radial cuts or incisions are made in the slab, spaced along the cavity edge to provide increased compliance of the slab material for reduced shear stress in the vicinity of the edge against the tissues of a person seated on the slab. In a third solution, the cushion slab comprises a thinner upper layer of more compliantly resilient material and a thicker bottom layer of less compliantly resilient material to reduce shear stress at the cavity edge.

In some cases it may be found desirable to cut or incise the upper seat surface in a grid pattern to a predetermined depth in at least two regions generally underlying the femoral head areas of a person seated thereon for increased compliance of the slab material in these regions.

It is also desirable to slope the forward edge of the cushion upwardly and rearwardly, away from the knees of a user for reduced pressure on the popliteal areas of a person seated thereon to avoid possible impairment of blood circulation to the lower legs. In the alternative the forward edge of the cushion may be cut or incised at spaced intervals to a relatively small depth for increased compliance of the slab material along the forward edge.

If the improved cushion is to be used on a sling-type seat such as in a wheelchair, or on softer, relatively yielding seats such as padded armchairs, it may be desirable to provide a substantially rigid baseboard under the cushion slab to support the same against deformation and sagging.

The cushion may further include a rounded protuberance rising from the upper seat surface forwardly of the ischial recess and intermediate the side edges for spreading apart the knees of a person seated thereon to prevent knocking of the knees. One or more wedges may be inserted under the cushion slab, between its undersurface and an underlying seat, for selectively and relatively elevating any portion of the slab seat surface thereby to rotate and reposition the pelvis of a person seated thereon.

In a second aspect of the present invention a compressible resilient body support pad with controlled spring-back has a slab of foamed resiliently compressible material generally sized, shaped and configured for use as a seat cushion, a pliant substantially air impermeable membrane closely enveloping the slab, and one or more apertures or other flow control elements such as valves in the enveloping membrane allowing restricted inflow of air into the foam slab, such that air is expelled from the foamed material when compressed under the weight of a body, the slab then molding to the shape of the compressing body and tending to remain in the compressed molded state under external atmospheric pressure due to the restricted inflow of air to the foamed material, but the slab slowly returning to an uncompressed state if unloaded. The foamed material may be a high resiliency polyurethane and the enveloping membrane can be made of vinyl. A rigid base board may be affixed to an undersurface of the cushion pad for use on a soft seating surface.

In a third aspect of this invention a pressurizable seat cushion with ischial relief comprises a baseboard having an upper surface bounded by a forward edge, a rear edge, and two sides. A number of pressurized cells or bladders are attached to the upper surface and arranged in rows extending between the forward and rear edges. The rows are spaced apart to define a central depression between the rows. The cells can be independently and selectively pressurized or filled by a fluid medium such as air, a gel or limited travel beads, such that the combined support characteristics of the cell rows is adjustable to a desired body support profile. The cells are also physically spaced and mechanically decoupled such that deformation of one cell under load is not significantly transmitted to an adjacent cell. The spacing between the cell rows is such as to provide body support primarily against the buttocks and thighs, and reduce or minimize pressure against the coccyx, anal, ischial and genital areas of a user. In particular it is desirable to space the rearmost cells in each row so as to define an ischial cavity for relieving pressure on the ischial tuberosity areas of a user. It may be advantageous to provide for variable adjustable spacing between some or all of the cells in the two rows so that the space between the rows, or at least their rear portions, can be optimized for the requirements of a particular user.

The cushion may also include a pump connected for pressurizing the cells and a sensor associated with one or more of the cells for sensing pressure exerted against the body of a person supported thereon. The sensor may be operatively interconnected with the pump for maintaining desired pressure levels on a seated body, for periodically modifying such pressure levels, or for cyclically variably pressurizing at least some of the cells thereby to achieve variations in local pressure applied to a body seated thereon and thus reduce the likelyhood of tissue damage such as pressure sores. The pump may also be arranged for variably pressurizing at least some of the cells at time intervals for repositioning the pelvis of a person seated thereon.

In a fourth aspect of this invention an improved peak-pressure sensor for diagnostic use with body support devices such as the improved cushions here disclosed comprises an inflatable envelope of pliable material, substantially pliable electrically conductive contact sheets affixed to opposing inner surfaces of the envelope in mutually facing relationship, conductors for electrically connecting the sheets to an alarm circuit; a fluid permanently sealed at a predetermined internal pressure to normally hold apart the contact sheets, the conductive sheets being movable into mutual electric contact by sufficient inward pressure applied locally to a sensing area on the exterior of the envelope. The envelope may consist of two pliable impermeable sheets sealed together along common edges.

The conductive contact sheets are thin metallic sheets in which portions are slit into narrow strips or ribbons, preferably within a central area of each sheet, the thin strips being held together by a common continuous periphery of the sheet, so that the sheets are made more readily compliant for movement with the envelope wall, to provide relatively large and substantially continuous electrical contact areas, and are responsive to local pressure applied within a small region of the sensing area for detecting excessive peak-pressure levels by actuating an alarm circuit connected to the contact sheets.

The minimum external pressure required to actuate such a sensor is determined primarily by the internal pressure of the pre-charged envelope. Two or more such sensors, each pre-charged to a different pressure, may be stacked for ascertaining, to an approximation, the pressure to which is subjected a given anatomical portion by a cushion or other body support device.

DETAILED DESCRIPTION OF THE PREFERRED EMBODIMENTS

Figures 1, 2, 3, 5A, 5B, 6, 7:
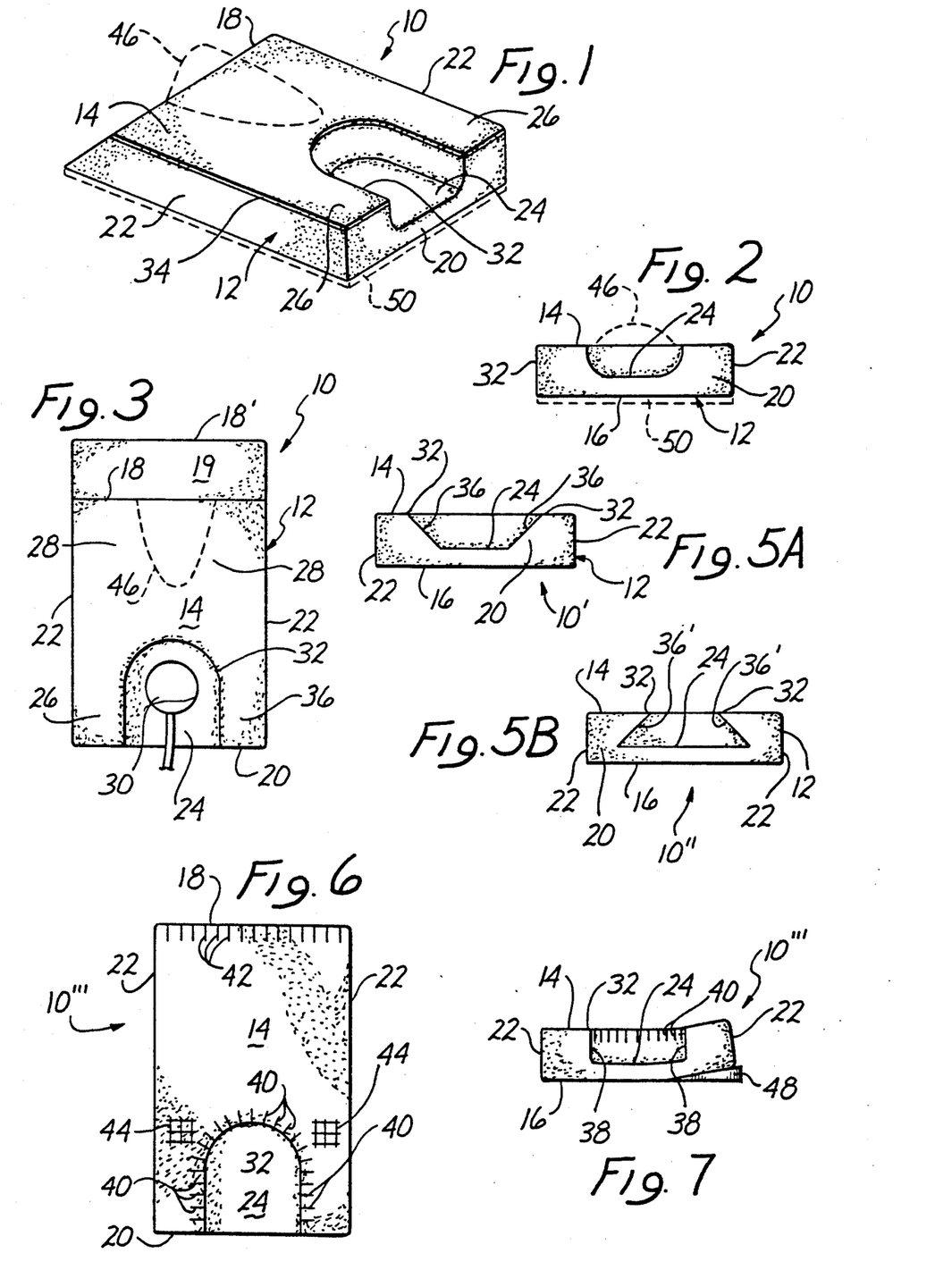
FIG. 1 is a perspective view of a seat cushion with ischial tuberosity relief according to one aspect of this invention.
FIG. 2 is a rear view of the cushion of FIG. 1.
FIG. 3 is a top plan view of the cushion of FIG. 1 showing also a peak pressure sensor installed in the ischial recess.
FIG. 5A is a rear view of an first alternate embodiment of the cushion of FIG. 1.
FIG. 5B is a rear view of a second alternate embodiment of the cushion of FIG. 1.
FIG. 6 is a top plan view of a third alternate form of the cushion of FIG. 1.
FIG. 7 is a rear elevational view of the cushion of FIG. 6 also showing one side of the cushion elevated by means of a wedge.

FIGS. 1, 2 and 3 illustrate an improved seat cushion 10 particularly useful for use by chair-bound individuals such as those having spinal cord injury. The cushion 10 includes a slab 12 of a resilient, compressible material such as a foamed synthetic material. The slab 12 is preferably rectangular with an upper supporting or seat surface 14, an undersurface 16, a forward edge 18, a rear edge 20 and two side edges 22. The slab 12 has in its upper surface 14, intermediate the two sides 12, an ischial recess or cavity 24 which is open at the rear edge 20 as illustrated, and which extends from the rear edge 24 forwardly towards the forward edge 18 approximately one third ($\frac{1}{3}$) of the length of the pad, at least four inches for children and seven inches for adults, as best seen in FIG. 3. The width of the recess 24, measured at the rear edge 20 is preferably about two fifths (2/5) of the width of the slab 12 between the two sides 22. The depth of the recess 24 at its central floor area is preferably one-half to two-thirds ($\frac{1}{2}$ to $\frac{2}{3}$) of the slab thickness which in a basic form of the improved cushion may be uniform throughout the supporting upper surface 14. The ischial depression 24 is dimensioned so as to leave substantial buttock supporting areas 26 laterally to the recess 24 and substantial thigh supporting areas 28 forwardly of the recess 24, as best seen in FIG. 3.

Figure 4A:
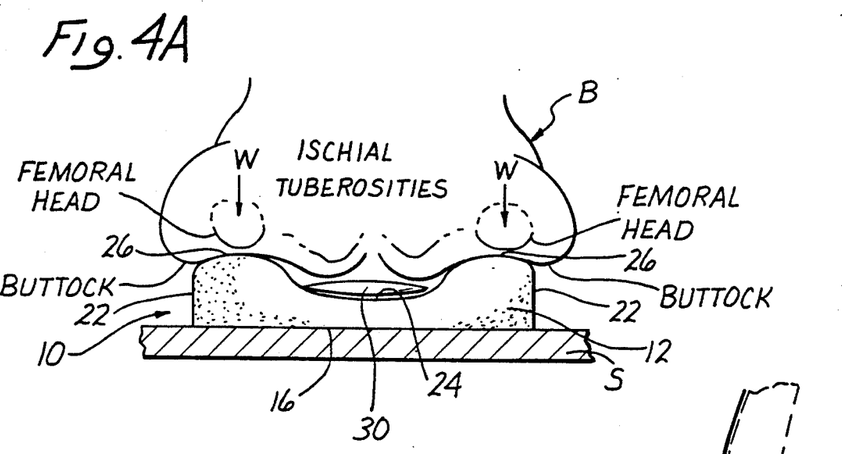
FIG. 4A is diagrammatic frontal illustration in elevational section of a human body supported on the cushion of FIGS. 1-3.
Figure 4B:
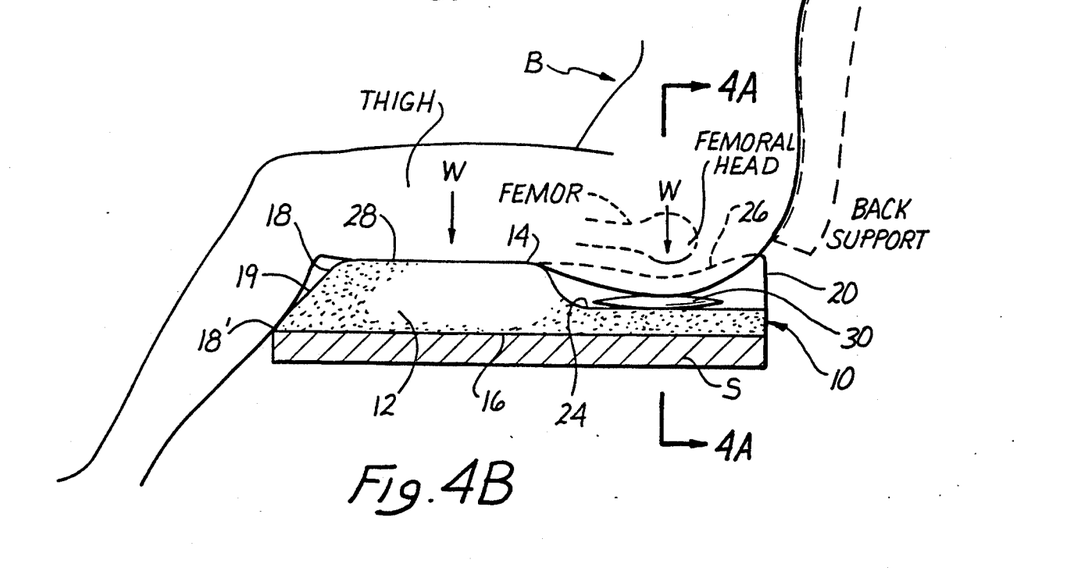
FIG. 4B is a side elevational view of a human body seated on the cushion of FIGS. 1-3, the cushion being shown in elevational section.

The improved seat cushion 10 is best used on a relatively hard and unyielding seat surface S such as a wheelchair sling seat, or any other seat or supporting surface S which is relatively hard in comparison with the foamed material of cushion slab 12, as illustrated in FIGS. 4a and 4b. As seen in FIG. 4a, an individual B is seated on the cushion 10 which itself is supported on seat S. The user's body B is shown in partial section taken in a vertical plane cutting through the femoral heads and ischial tuberosities of the body B as well as transversely through the cushion slab 12 approximately along line 4a—4a in FIG. 4b. The dimensioning of the cushion 10 relative to the anatomy of body B is illustrated. The width of the ischial depression 24 is such as to generally receive and accommodate the ischial tuberosity area of body B. This area has a width which is rather uniform from person to person and tends to be approximately 4 to 4.5 inches A preferred adult width for the ischial recess 24, measured at the rear edge 20 is 7 inches, providing about one inch clearance to either side of the ischial tuberosities. This clearance is significant in that it moves the upper edge of the cavity 24 sufficiently away from the tuberosities to minimize lateral pulling and shear stress on the skin and soft tissues covering the tuberosities. The ischial area of body B when properly fitted to cushion 10 therefore tends to hang within the depression 24 while the weight W of body B is shifted laterally onto the buttocks and fleshy underside of the thighs. In particular, a significant portion of the individual's weight will be borne by the area of the buttocks underlying the femoral heads, which along with their pelvic sockets form a substantial bony protuberance on each side of the pelvis. The femoral support areas 26 of the cushion 10 support the femoral head areas of body B, while the thighs are supported by areas 28 of the cushion surface 14. The overall dimensions of the slab 12 may vary between 16 and 22 inches in both length (distance between forward edge 18 and rear edge 20) and width (distance between sides 22) depending on the size of the individual being fitted with the pad. The height or thickness of the pad between upper surface 14 and under surface 16 is also selected for the particular weight of the body B. The compressibility of the foam material comprising the slab 12 is likewise selected to provide proper weight distribution by shifting pressure away from the ischial tuberosity area in the manner just described. Proper fitting of the pad to a particular individual advantageously includes the use of a peak-pressure sensor 30 disposed on the floor of the ischial recess 24 as illustrated in FIGS. 3, 4a and 4b. A preferred construction of the peak pressure sensor is described below in another aspect of the present invention. Generally, the sensor 30 is a disc shaped envelope which is pre-charged to a known internal pressure, and contains electrical contact elements normally spaced apart by the pressurized medium. When positioned as shown, underneath the ischial tuberosity area of body B the patient can be properly fitted with a pad 10 which will be effective in shifting pressure away from this sensitive area. If excessive pressure is applied to the tissues underlying or adjacent the ischial tuberosities, such pressure levels can be detected by the peak pressure sensor 30 through a suitable signaling or alarm system connected to the sensor 30, such as will be described below. Detection of excessive pressure levels against the ischial tuberosity area of the user calls for a refitting of the pad to a less compliant foam material of slab 12 or in the alternative to a thicker slab 12 with a deeper recess 24, or a combination of these variables. The compliance of synthetic foams, such as polyurethane foams, is typically given as the ILD (Indentation Load Deflection) value of the particular foam, which can vary widely and is an industry standardized measure of the fight-back force or compliance of the foam material. For slab 12 foams having an ILD value of at least 100 have been found acceptable for adult users of at least average weight. It must be understood however that foam ILD is to be selected with regard to the size, weight and other anatomical and personal considerations and requirements of an intended user or group of users, and this invention is therefore not restricted to foam materials of a particular ILD.

It will be noted that the ischial depression 24 is open at the rear edge 20 so that a properly fitted cushion 10 relieves pressure loading on the tail-bone area of body B in a slouching position of the user, as will be apparent from FIG. 4b, slouching typically implying rearward tilting of the pelvis with a consequent downward rotation of the tail bone against the cushion 10. The open recess 24 allows such slouching without attendant loading of the skin and tissues covering the tail-bone skeletal structure and thus the cushion is effective in protecting this area as well against soft tissue damage and ulceration. A still further benefit of the rearward opening of the ischial depression 24 resides in the fact that the cushion 10 does not press against an restrict the posterior vascular system, i.e. the blood vessels which run down along the lower back and inner buttocks to feed the lower extremities, as might be the case, for example, in a ringlike cushion. Yet another advantage of the open cavity 24 relies on the anatomical fact that the center of gravity of body B is normally about two inches behind the ischial tuberosities, and by moving the cushion support areas away from the tuberosities and at least partially forwardly to the thigh areas, gravity is allowed to pull down the rear of the pelvis with the result that a forward-tilted pelvis is rotated to a more correct, erect position. This in turn yields benefits by straightening the spine for relief of lower back pain caused by squeezing together and friction of the vertebrae.

A further concern in any resilient pad, cushion or similar body support device is the control of shear stress at any cavity or side edges of the cushion which normally make contact with the body being supported. Such shear stress occurs at the edge transition between a supporting surface and a cavity such as the transition 32 from the supporting surface 14 into the ischial recess 24. A sharp transition at such an edge 32, even if the material is relatively compliant, tends to cut into the skin and underlying soft tissues of the supported body B when fleshy portions of body B are extruded into the cavity by weight of the body, and are particularly stressed at the edge of the cavity. In order to avoid or minimize possible damage to the soft tissues in contact with the cushion 10 of this invention, it is therefore desirable to control shear stresses at the edge 32 of the ischial recess 24. A first solution to this problem, illustrated in FIG. 1, is to provide the slab 12 with a relatively soft, thinner top layer 34 which, in particular, extends to the edge 32 of the recess 24, and desirably also to the forward, rear and side edges of the top surface 14. The softer covering layer 34 provides for shear stress relief at the edge 32 to reduce the likelihood of injury to the soft tissues at this transition into the recess 24. By way of example, a polyurethane foam of 70 ILD and a weight of 4 lbs/ft3 may be selected for the top layer, while a 120 ILD foam of 6 lbs/ft3 may be used for the bottom layer.

A second solution to the same problem is illustrated in FIG. 5a where a cushion 10' has an ischial cavity 24 where the cavity side walls 36 have been sloped inwardly to the center of the ischial recess at a preferred angle of 45' to the top surface 14. The sloping surfaces 36 provide a more gradual transition into the cavity and assist in supporting any soft tissues of body B which extrude into the cavity 24 immediately adjacent the cavity edge 32 thereby reducing shear stress at this edge transition.

Yet another solution to the same problem is suggested in FIG. 5b in cushion 10,, where the side walls 36, of the ischial recess 24 are reverse sloped i.e. outwardly from the cavity 24 in a downward direction, at a preferred angle of 45 degrees to the supporting upper surface 14, undercutting the cavity edge 32. This reverse sloping of the wall surface 36 provides for a gradation in compliance of the foam material in the vicinity of edge 32, the regions of surface 14 nearest to the edge 32 most readily yielding under downward pressure exerted by a body B resting on surface 14. Those regions of the supporting surface 14 nearest the edge 32 are least supported and more readily yield under a load. The compliance of the surface 14 nearest the edge 32 is thus a function of the slope of the side wall 36' and the distance from the edge 32. The shallower the slope, i.e, greater undercutting of edge 32, the greater the compliance at the edge 32. It is understood that in FIGS. 5a and 5b the slope of the cavity side wall surface 36 is substantially uniform along the entire edge 32.

Yet a fourth solution to shear stress control at edge transitions on surface 14 is illustrated in FIGS. 6 and 7 in alternate cushion 10''' where the ischial cavity 24 has substantially perpendicular side walls 38 to the supporting upper surface 14 and undersurface 16 . Shear stress control is provided along cavity edge 32 by relatively small incisions 40 into the foam material at the edge at evenly spaced intervals along edge 32. Each incision 40 is generally perpendicular to the edge 32 as shown in FIGS. 6 and 7 and collectively the incisions are radial to the cavity 24. The cuts 40 preferably are generally triangular cuts with edge 32 at the outer apex of the triangle, and two sides defined by incision lines on surface 14 and side wall 38 respectively, the base of the triangular cut being internal to the foam material and connecting the surface 14 with side wall 38. The effect of such regular slicing or cutting of the edge 32 is to locally increase the compliance of the foam material by isolating the individual's foam segments between adjacent cuts 40 from lateral strain forces when a compressive force is applied to each segment.

It will be understood that two or more of the just enumerated four possible solutions to shear stress control at edge transitions may be adopted and combined in a particular cushion configuration.

It is further desirable to provide pressure relief at the forward edge 18 of the cushion 10 where, as shown in FIG. 4B, the cushion may tend to press against the back of the knees. This area carries blood vessels supplying the lower legs and sustained pressure against the skin here is undesirable as a possible impediment to proper vascular circulation. In the cushion 10 of FIGS. 1-4b, relief is provided in this area by sloping the forward face 19 of the slab 12 at a preferred angle of about 45 degrees from the forward edge 18 of the supporting upper surface 14 forwardly towards the lower forward edge 18' of the undersurface 16, as shown in FIGS. 1, 3 and 4b. The upper edge 18 is consequently recessed away from the knees to avoid pressing or rubbing against the same. An alternate approach to providing pressure relief to the back of the knees is illustrated in FIG. 6 and is an extension of the already described approach to controlling stress along the cavity edge 32: namely, relatively small incisions or cuts 42 are made at spaced intervals along the edge 18 as shown in FIG. 6 to locally increase compliance of the foam material at edge 18 in the same manner as has been described in connection with cuts 40 along cavity edge 32.

In some instances, it may be desirable to provide additional shear stress control over selected regions of supporting upper surface 14 or perhaps over the entire surface 14. Shear stress on skin and soft underlying tissues can occur even on a flat yielding support surface when tissues covering a bony protrusion are pulled to the sides of the protrusion as the protrusion tends to push through the covering tissues into the supporting surface under the weight of the body. Localized stress relief may be particulary desirable in areas 26 which directly underlie the femoral head regions of the supported body B. In FIG. 6 such localized stress relief is provided by cutting the surface 14 in a grid pattern defining arrays 44 of rectangular blocks which are interconnected by a common underlying layer of foam. The degree of compliance achieved by such gridding of the foam surface will depend on the depth of the cuts and the spacing of the cut lines, all other factors being equal. The reason for the increased compliance is the same as with the treatment of edge 32 in FIGS. 6 and 7. This treatment of the supporting surface 14 may be localized as shown in FIG. 6, or in the alternative may extend over the entire surface 14.

A feature optional to the cushions of FIGS. 1-7 is the provision of a knee spreader protuberance 46 shown in dotted lining in FIGS. 1-3. Such a protuberance may be molded integrally with the slab 12 or may be a separate element adhesively or otherwise affixed to the surface 14 adjacent the forward edge 18, forwardly of the ischial depression 24 and intermediate the cushion sides 22. The dimensions of this protuberance 46 are not critical and even a relatively low protuberance of one or two inches in height will be helpful in spreading apart the knees of the an individual seated on the cushion. The provision of this optional protuberance 46 may be indicated in cases of certain individuals in whom the thighs show a tendency to roll inwardly when seated so that the insides of the knees tend to knock against each other. Such knocking over a long period of time also is potentially damaging and is desirably prevented by the simple means just described.

The localized, selective cutting of a foam slab 12 may be also instrumental in the planned repositioning of the pelvis of a user. For example, persons having a naturally tilted pelvis may be aided by increasing the compliance of the surface 14 on one side of the ischial recess 24 so as to achieve a left or right hand tilting of the pelvis by for example, deeper grid slicing of the foam surface in for example, one femoral array 44 shown in FIG. 6. Persons with a forward tilted pelvis can be assisted by increased compliance of the surface 14 on both sides of the recess 24 near the rear edge 20, so as to cause rearward rotation of the pelvis when supported by the cushions of FIGS. 1-7. Pelvic repositioning may also be achieved through the use of a solid wedge 48 inserted under one side 22 of the cushion 10''' to elevate the cushion along that side as in FIG. 7.

Still another option for use with the cushions of FIGS. 1-7 is the provision of a rigid base board 50 shown in phantom lining in FIGS. 1 and 2, consisting of a sheet of stiff preferably thin material such as a sheet of plywood or the like, preferably adhesively fixed to and coextensive with the undersurface 16, for the purpose of maintaining the effectiveness of the cushion when used on a yielding, relatively soft seat, and especially a sling seat in a wheelchair made of pliable material which tends to hammock between two supporting side rails and would otherwise cause the foam slab 12 to conform to the sagging seat surface and consequently impair its usefulness.

The shape of the ischial recess 24 in top plan view is wider at the rear edge 20 than at the forward extremity of the recess, and a generally semi-elliptical or semi-ellipsoid shape of the edge 32 is preferred, but this shape may also be trapezoidal or even generally triangular with the apex pointing forward towards the edge 18 and the base coextensive with the rear edge 24. In a particular individual, the forward extent of the recess 24 should be sufficient to underlie the genitalia of the intended user so as to avoid pressing against the same, and generally a dimension of approximately 7 inches from the rear surface 20 along the center of the recess 24 is acceptable for this purpose.

Figure 8:
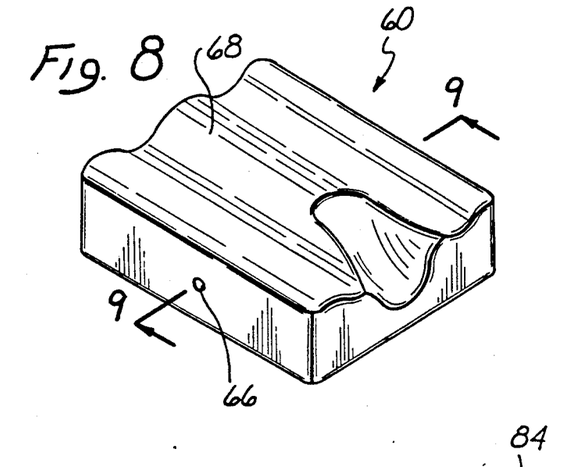
FIG. 8 is a perspective view of a moldable cushion with controlled spring-back according to another aspect of the present invention.
Figure 9:
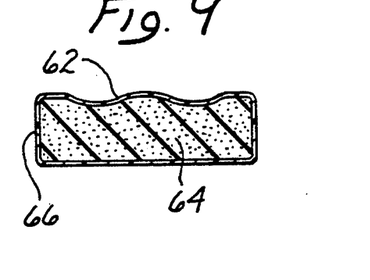
FIG. 9 is an elevational cross-section taken along line 9—9 in FIG. 8.

Turning now to FIGS. 8 and 9, another aspect of the present invention is directed to a compressible, resilient, body support such a cushion, pad or mattress featuring a controlled degree of spring-back of the resilient material. This spring-back may be effectively reduced or even suppressed, for example in a cushion 60 made of resilient foamed synthetic material by encasing the foam material in a compliant air-impermeable membrane closely fitted to all outer surfaces of the foam cushion. A thin sheet of vinyl, or other synthetic thin sheet material may be adapted for this purpose, by forming a casing or envelope 62 closely fitted to all surfaces of a foam block 64, as shown in FIG. 9. One or more small holes 66 are provided in the air-impermeable membrane 62. The foam material 64 contains a substantial volume of air in minute cellular cavities distributed throughout the foam block. When a weight is placed on the foam material, such as a body seated on the cushion surface 68, the foam material is compressed and a portion of its air content is squeezed out and expelled, allowing the block 64 to conform to the shape of its load and in the case of a cushion, to mold itself to the shape of a human body resting on it. If the air expelled foam the compressed foam material is prevented from reentering the foam block 64, the effect is akin to a vacuum molding of the cushion surface in that external atmospheric pressure bearing on all outer surfaces of the foam block cannot be equalized by air re-entering the foam mass so that atmospheric pressure will counteract the resilience of the foam material and keep it from expanding and returning to its original, unloaded shape. The closely fitted impermeable membrane 62 operates to close off air flow into or from the foam mass except as allowed by air flow control openings 66 or equivalent valve devices. A small opening 66 such as shown in FIG. 8 e.g. a one-sixteenth (1/16) to one-eight (⅛) inch diameter hole, is sufficient to allow air egress from the foam block 64 when it is compressed under the weight of a person's body. The cushion 60 will mold to the shape of the anatomy supported by surface 68 as the air is expelled through the air flow control opening 66. Once compressed under its load however, the cushion will show little or no spring-back from its compressed molded condition because of the restricted in-flow of air into the foam mass. The cushion will have no significant "fightback" yet be easily moldable and adaptable to repositioning of the person's body on its surface 68 even while compressed. What will be lacking is the tendency of the foam to spring back in response to minor changes and shifts in position of the person sitting on the cushion, which is annoying and detracts from the comfort of the user. Once unloaded for a significant period of time however, the cushion 60 will gradually expand as air is admitted in controlled flow through the opening 66 or equivalent valve elements provided for this purpose, and thus gradually return to its original, uncompressed size and shape. This is desirable so as to, for example, allow the cushion to then properly mold to a different user.

Figure 10:
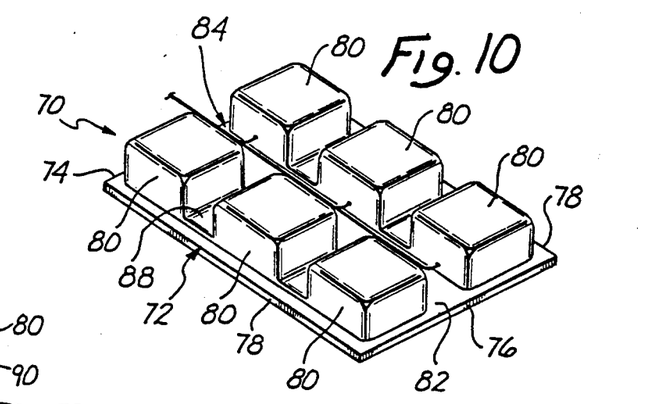
FIG. 10 is a perspective view of an independently pressurizable multi-cell seat cushion according to still another aspect of this invention.
Figure 11:
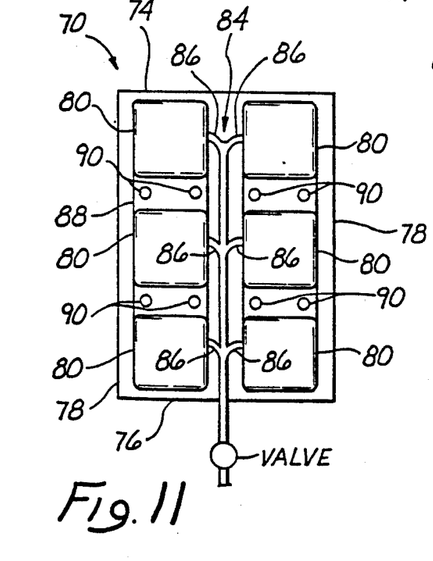
FIG. 11 is a top plan view of the cushion of FIG. 10.
Figure 12:
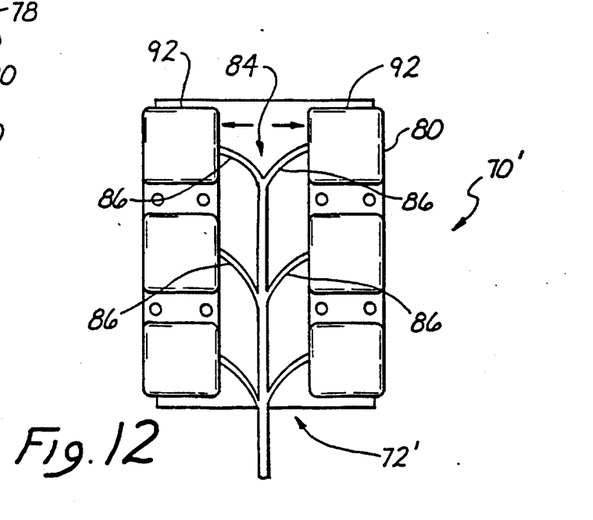
FIG. 12 is a top plan view of a seat cushion as in FIG. 10 modified for variable spacing between the pressure cell arrays.

Turning now to FIGS. 10 through 12, still another aspect of the present invention relates to a cellular cushion 70 which includes a rectangular relatively rigid baseboard 72 which may be of masonite, plywood or other suitable equivalent material, dimensioned generally for use on another seat support such as a wheelchair, armchair and the like. The baseboard has a front edge 74, a rear edge 76 and two side edges 78. Two rows 92, each including three individual separate cells 80 are arranged and secured to the upper surface 82 of the baseboard 72, extend between the forward edge 74 and rear edge 82. The two rows 92 of cells 80 are laterally spaced apart from each other so as to leave an intermediate channel or longitudinal depression 84 which extends the full length of the baseboard between the forward and rear edges. The cells are also spaced apart from each other in a longitudinal direction so as to accommodate some lateral expansion and flattening of the individual cells 80 when loaded with the weight of a person seated thereon. Each cell 80 is individually pressurizable and closed from any other cell 80. Each cell 80 is provided with an individual inlet conduit 86, and six such conduits 86 are led along the central depression 84 to the forward edge 74 of the baseboard terminating in six separate valves, one controlling the admission of pressuring medium into each cell 80. The valving of the inlet conduits 86 may be arranged in different ways as may be convenient.

The individual bladders or cells 80 are made of thin vinyl sheet or other synthetic air-impermeable sheet material such as polyurethane or neoprene, among other possible suitable materials. Each cell 80 is generally rectangular, preferably with somewhat rounded edges, each with a base with a planar top surface and flange 88 which is attached to the baseboard 72 by means of fasteners 90, as best seen in FIG. 11. The baseboard 72 may be about 15 inches in length and up to 15 inches in width. It is presently preferred to make each cell 80 about 6 inches in transverse width i.e. the dimension measured between the baseboard sides 78, about 3 ½ inches along the longitudinal dimension of the baseboard i.e. between the forward edge 74 and rear edge 76, and about 2 inches in height above the baseboard surface 82. The cells 80 in each row 92 are spaced about one inch from each other. The precise dimensions of the individual cells 80 as well as their spacing are not critical and may be varied to suit the anatomy and weight of a particular individual being fitted with cushion 70. The longitudinal depression 84 is about seven inches wide, at least between the two rearmost cells 80 in each row 92. The lateral spacing between the rearmost cells 80 in each row may advantageously be adjustable. This spacing of the cells adjacent the rear edge 76 emulates the geometry of the ischial cavity 24 in the cushion 10 of FIGS. 1-3, and provides the attendant benefits already described in connection with the same.

In a presently preferred form of the cushion the pressurizing medium in each cell 80 is compressed air. It is contemplated however, that other pressurizing media may be substituted such as for example, an inert gel or a liquid, either of which would be substantially incompressible while retaining nearly all the moldability and fluidity of compressed air. Still another alternative is to fill the individual cells 80 with limited-travel solid beads which would then offer limited compressibility of the cells 80 coupled with substantial moldability, while reducing the complexities of fluidic sealing of the cells 80.

Previously known pressurized or fluid-cell cushions have suffered of a shortcoming in that the cushion was either constructed of a single pressurized cell or when divided, the individual cells were not independent by either being fluidically in communication or being physically coupled with each such that a pressure increase in one is transmitted physically to adjacent cells in a ripple effect. The cell arrangement of the novel cushion 70 is such as to decouple the individual cells 80 both fluidically as well as physically from pressure variations in each other. The spacing between individual cells is desirably both in the longitudinal direction within each row 92 as well as transversely such that deformation of the cell under a load does not cause a significant pressure variation or fluctuation in an adjacent cell.

The provision of independent pressure lines 86 to each cell 80 yields the unique ability in cushion 70 to provide a desired support profile by adjusting the relative pressure levels in each cell 80, especially each cell along the longitudinal rows 92. For example, rotation of a tilted pelvis can be easily achieved by an appropriate pressure differential between cells 80. If the pelvis requires tilting to a more erect vertical position for example, this can be achieved by providing somewhat greater pressure in the middle cells 80 in each row relative to the rearmost cells. Various adjustments of the individual anatomy can therefore be readily accomplished. Furthermore, it is possible to take into account comfort preferences of each individual by making appropriate changes in the relative pressurization of the cells 80, which can be easily changed and adjusted.

FIG. 12 shows one alternative form of the cushion 70 wherein the two rows 92, each including three cells 80 similar to the cells in FIGS. 10 and 11, are mounted on movable base strips to the baseboard 72' in such a manner as to allow variable lateral spacing of the strips 92 so as to provide adjustablity of the width of the longitudinal depression 84 so as to accommodate different anatomies and comfort preferences. The adjustability of the depression width can be achieved in various ways such as for example, fitting the fasteners 90 into transverse slots in the baseboard 72' so as to allow a limited degree of lateral movement of each row 92 or each cell 80 preferably independently of each other, or even by providing for limited rotation of the entire rows 92 about the center cell 80, so as spread the rows at one end or the other, or a combination of such arrangements.

Figure 13:
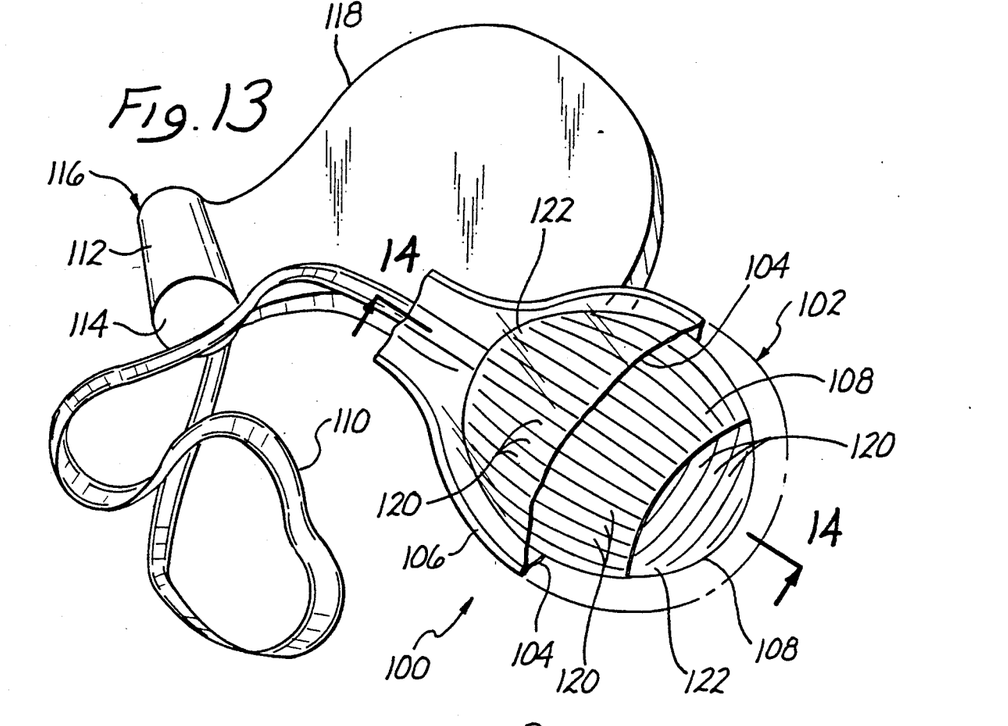
FIG. 13 is a perspective view partly broken away of a pre-charged pneumatic peak-pressure sensor unit for use with body support devices and cushions.
Figure 14:
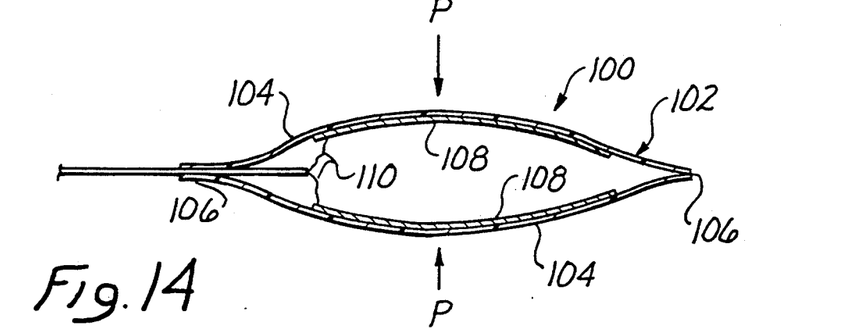
FIG. 14 is a cross-section of the pneumatic switch element taken along line 14—14 in FIG. 13.
Figure 15:
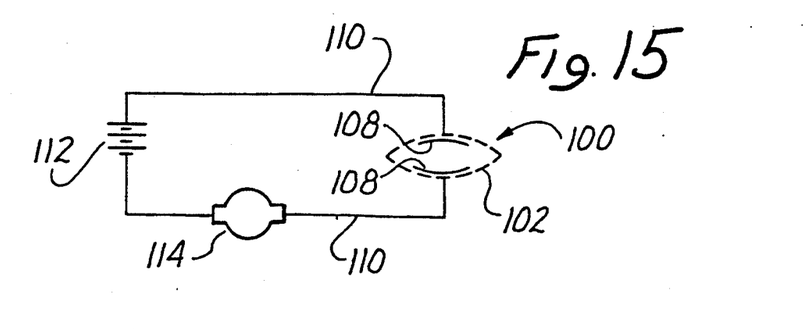
FIG. 15 is an electrical schematic of the pre-charged pneumatic peak pressure sensor of FIG. 13.

Turning to FIGS. 13-15, yet another aspect of the present invention relates to improvements in diagnostic devices for use in fitting cushions, pads or other body support devices to the needs of particular individuals. FIGS. 13 and 14 show a pneumatic peak pressure sensor 100 which includes an outer envelope 102 made up of two air impermeable sheets 104 joined along a common edge 106. For example, two generally circular sheets of thin vinyl may be heat sealed along their periphery 106 to make up an air tight envelope 102. Two thin metallic contact sheets 108 are adhesively affixed to opposite inner surfaces of the envelope 102, as shown in FIG. 14, one contact sheet 108 to the opposing inner surfaces of each envelope sheet 104. A pair of electrical conductors 110 are connected, one to each contact sheet 108 within the envelope 102 and led through an air tight passage to the exterior of envelope 102. The interior of the pneumatic envelope 102 is then pressurized, as by compressed air, to a predetermined pressure level which can be determined empirically as being sufficient to maintain the contact sheets 108 in normally spaced apart relationship, as shown in FIG. 14 against a pressure P acting on the exterior of the envelope 102 tending to bring the contact plates 108 together. This pressure P is then the peak pressure which it is considered unacceptable to exceed against any portion of a particular cushion user's anatomy. When such pressure is exceeded against the exterior of the envelope 102, some portions of the plates 108 are brought into electrical contact, which condition can be used to actuate a suitable alarm in a simple circuit such as depicted in FIG. 15 comprising the pneumatic switch 100 contacted in series to a battery 112 and audible alarm or buzzer 114. The entire alarm circuit may be assembled in a compact arrangement shown in FIG. 13 where both battery 112 and buzzer 114 are housed in a small housing 116 which is physically attached to a case 118 in which the envelope 100 is normally stored when not use, and conductors 110 suitably insulated and physically protected interconnect the housing 116 to the envelope 100.

One novel feature in the peak pressure sensor 100 is the precharging of the envelope 102 to a sufficient internal pressure, e.g. 10 mm air pressure above sea level atmospheric, so as to detect contact of the plates 108 as indicative of a given external pressure on the envelope 102. This precharging is a permanent internal pressurization of the envelope so as to provide a convenient lightweight and ready to use pneumatic sensor which can be easily inserted as necessary between the user's anatomy and the cushion or other support device, for example, as indicated in FIGS. 3, 4a and 4b for detecting excessive pressure levels and to allow proper fitting of the cushion to the user's needs.

A further improvement in the peak pressure detector 100 is the use of metallic contact sheets 108, made preferably of thin copper sheet, e.g. about 3 mil thick adhesive backed copper sheet, and which are slit into relatively thin ribbons or strips 120, desirably no more than ¼ inch wide and preferably about ⅛th inch wide, over a large central portion of each sheet 108. The ends of the strips 120 are interconnected by a common uncut periphery 122 of each sheet 108. The resultant contact sheets 108 are highly pliable and flexible for flexing movement together with the envelope walls 104, which may be of 10 mil thick vinyl sheet, in response to pressure differences across these walls. Furthermore, the increased pliability of the electrical contact sheets 108 allows detection of locally applied pressures, i.e. pressures applied to a small portion of the exterior surface of the envelope sheets 104 which pressure is sufficient to locally indent the envelope wall 104 and is not distributed over the entire surface of the wall 104. As a result, the highly pliable contact sheets used with relatively large e.g. two inches or more in diameter envelopes 102 produce a sensitive peak pressure detector as opposed to an average pressure detector. Still further, the slit sheets 108 provide for virtually continuous electrical contact at any point along the surface as opposed to previously used wire grids or discrete contact points spaced apart in comparable switches, which can provide inferior resolution and less reliable contacts. The pneumatic switch or sensor 100 can be made in two sizes found useful, one a smaller envelope measuring about 1 inch by ⅝ths inch, and a larger size measuring about 4 by 2 inches in envelope size, the copper sheets being slightly smaller in both cases to avoid false contact at the envelope edges. The smaller sensor is useful at anatomical locations where the pressure point of concern can be visualized and is readily accessible, as under a heel. The larger sensor size is preferable for use under larger, heavier portions such as the buttocks or seat areas where the bony protuberances are not readily visualized and access is difficult as under a sitting or reclining individual.

It may be convenient in some cases to stack two or more sensors 100, each precharged to a different internal pressure so as to determine to a degree of approximation peak pressures falling within the pressure range represented by the stacked pressure sensors 100. A number of envelopes 102 may be affixed together adhesively or otherwise into a detector assembly for diagnostic use in a manner similar to the use of a single envelope detector 100. In a stacked arrangement, the envelope 102 of lowest internal pressure will make electrical contact first and so on up to the highest pressure envelope. Each envelope is connected to a corresponding signally device which are thus triggered sequentially from lowest pressure to highest pressure indication.

While particular embodiments of each aspect of the invention have been described and illustrated for purposes of example and clarity, it will be understood that many changes, substitutions and modifications to the same will become apparent to those possessed of ordinary skill in the art without departing from the spirit and scope of the invention as defined in the following claims.

What is claimed is:

1. A seat cushion comprising:
    a baseboard having an upper surface bounded by a forward edge, a rear edge, and two sides
    a plurality of independently pressurized bladders attached to said upper surface and arranged in rows extending between said forward and rear edges, said bladders being of substantially rectangular shape with four sides and a planar top surface each, each bladder having a base flange attached to said base board, said bladders in each of said rows being spaced from each other at said upper surface by a distance sufficient to prevent mutual deformation under a load acting on said top surface;
    said rows being spaced apart at least adjacent to said rear edge by about seven inches from each other to define a central depression between said rows for accommodating the ischial tuberosities of a person seated thereon; and
    means for independently and selectively pressurizing each of said bladders whereby the combined support characteristics of said bladders is adjustable to a desired support profile.

2. The cushion of claim 1 wherein said bladders are pressurized by inflation with air.

3. The cushion of claim 1 wherein said bladders are pressurized by a fluid medium.

4. The cushion of claim 1 wherein said bladders are pressurized by a filling of solid limited travel beads.

5. The cushion of claim 1 wherein the spacing between said rows on said baseboard is adjustable.

* * * * *